(12) United States Patent
Meyer-Clasen

(10) Patent No.: US 11,399,972 B2
(45) Date of Patent: Aug. 2, 2022

(54) THERAPY GLOVE AND FIXING SPLINT FOR A THERAPY GLOVE

(71) Applicant: Petra Meyer-Clasen, Villingen-Schwenningen (DE)

(72) Inventor: Carsten Meyer-Clasen, Koenigsfeld (DE)

(73) Assignee: Petra Meyer-Clasen, Villingen-Schwenningen (DE)

( * ) Notice: Subject to any disclaimer, the term of this patent is extended or adjusted under 35 U.S.C. 154(b) by 312 days.

(21) Appl. No.: 16/699,026

(22) Filed: Nov. 28, 2019

(65) Prior Publication Data

US 2020/0170824 A1 Jun. 4, 2020

(30) Foreign Application Priority Data

Nov. 30, 2018 (DE) .......................... 102018130567.2

(51) Int. Cl.
*A61F 5/10* (2006.01)
*A41D 19/015* (2006.01)

(52) U.S. Cl.
CPC .......... *A61F 5/10* (2013.01); *A41D 19/01588* (2013.01)

(58) Field of Classification Search
CPC .. A61F 5/013; A61F 2/583; A61F 5/10; G06F 3/014; G06F 3/016; A61B 5/0022; A61B 5/6806; A61B 5/225; A41D 19/0158
See application file for complete search history.

(56) References Cited

U.S. PATENT DOCUMENTS

| 3,170,460 A | * | 2/1965 | Stilson ................ A61F 5/05875 602/22 |
| 4,781,178 A | * | 11/1988 | Gordon ................. A61F 5/0118 602/22 |
| 5,453,064 A | * | 9/1995 | Williams, Jr. ......... A63B 23/16 2/161.1 |

FOREIGN PATENT DOCUMENTS

| DE | 102005014470 B3 | 9/2006 |
| DE | 202007002380 U1 | 4/2007 |
| DE | 202011104828 U1 | 9/2011 |
| DE | 102016116015 A1 | 12/2017 |

* cited by examiner

*Primary Examiner* — Ophelia A Hawthorne
(74) *Attorney, Agent, or Firm* — Kriegsman & Kriegsman

(57) ABSTRACT

A therapy glove and a fixing splint for fixing at least one finger with a glove, having at least one fingerstall going outwards from the central region, in which the finger to be fixed can be accommodated, having at least one fixing splint, which has a main splint section and at least one finger splint section arranged on it, having at least one fixing pocket arranged on the fingerstall, into which the finger splint section can be inserted, having a detachable fastener on every fingerstall which has a fixing pocket, to adjust a contact position of the finger in the fingerstall to the finger splint section.

12 Claims, 3 Drawing Sheets

THERAPY GLOVE AND FIXING SPLINT FOR A THERAPY GLOVE

Figure 1:
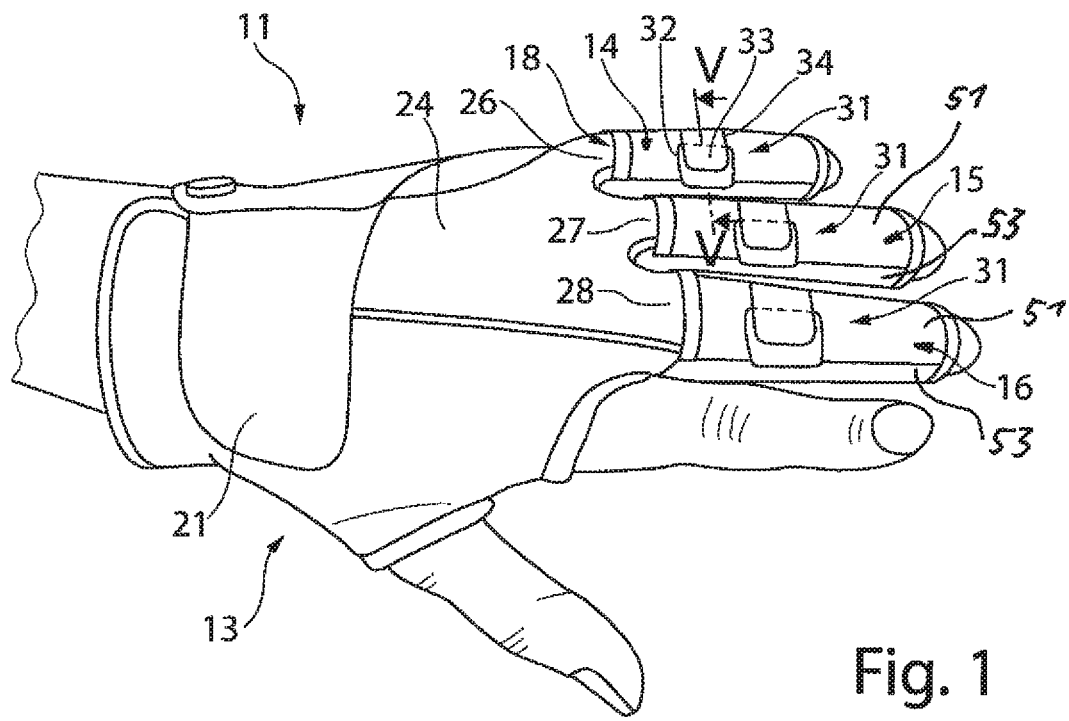

The invention relates to a therapy glove for fixing at least one finger and a fixing splint for such a therapy glove.

A therapy glove for fixing at least one finger is known from DE 20 2007 002 380 U1. Such therapy gloves are in particular used at night to stretch at least one finger in the case of a Dupuytren disease or in the case of a Dupuytren node attack. Such a therapy glove comprises a central region, which encloses the back of the hand and the palm of the hand. Going outwards from the central region, fingerstalls are provided in which the respective finger to be fixed can be accommodated. The therapy glove has a fixing splint, which has a central support region and individual finger splint sections going outwards from it. For fixing the fixing splint on the therapy glove, fixing pockets are provided on the fingerstalls, in which the finger splint sections are applicable. In addition, a detachable VELCRO® hook-and-loop fastener is provided in the central region, in order to detachably fix the main splint section to the central region of the glove. This arrangement makes it possible for the finger accommodated in the fingerstall to be fixed in a therapy position relative to the back of the hand. Since the fingerstalls consist of a breathable and flexible material, the extended position of the finger cannot be completely maintained.

In addition, a therapy glove for fixing at least two fingers is known from DE 20 2011 104 828 U1. This therapy glove comprises a glove having two fixing splints which can be arranged on it. A first fixing splint serves to position the little finger, the ring finger and the middle finger in an extended position. The second fixing splint extends between the index finger and the thumb. The fixing splints are also detachable by means of the VELCRO® hook-and-loop fasteners and removably connected to the glove. In this embodiment, the fixing splint is assigned to a palm of the hand. This fixing glove has the disadvantage that the extended position cannot be adjusted or maintained.

The invention is based on the object of proposing a therapy glove and a support splint for a therapy glove, with which an improved therapy is enabled. This object is solved by means of a therapy glove, in which each fingerstall, which has a fixation pocket for accommodating a fixing splint, is provided with a detachable fastener, through which a contact position of the finger in the fingerstall can be adjusted to the finger splint section. This detachable fastener allows the finger to be directly pressed against the splint, or positioned against it. This attached position of the finger to the support splint can be maintained by means of the fastener.

It is preferably provided that the fingerstall is formed from an elastically flexible material at least in sections, and the fixing pockets arranged on the fingerstall consist of an inelastic material, preferably in contrast to the material of the fingerstall. This design has the advantage that a defined accommodation of the finger splint or finger splint sections is enabled in the respective fixing pockets. On the other hand, the fingerstalls which are made of an elastically flexible material at least in sections make putting on the therapy glove easy. Advantageously, the cross-section of the fingerstall formed with the elastically flexible material at least in sections is formed as a half or a whole size bigger than this is provided in the region of the palm of the hand.

Furthermore, it is preferably provided that the fingerstall has a region made of an inelastic material opposite the fixing pocket, said region being oriented towards the inner side of the hand or to the outer side of the hand and an elastically flexible region is formed between the inelastic region of the fingerstall and the fixing pocket respectively. Thus the regions facing the outside and the inside of the hand, which are formed by the finger pocket and the inelastic region of the fingerstall, can be designed as robust and resistant, whereas the intermediate regions are elastically flexible, such that, in turn, the therapy glove can be put on easily. After the therapy glove has been put on more easily, the contact position of the finger in the fingerstall in relation to the finger splint section can be defined by the detachable fastener on the fingerstall. The initially enlarged free recess in the fingerstall for putting on the therapy glove more easily, due to the elastically flexible region, can be reduced in circumference by the detachable fastener. Depending on the therapy, the finger thus in turn lies firmly on the finger splint section.

Furthermore, it is preferably provided that the detachable fastener is generally provided in the region of the first or second phalanx or in the region of the joint between the first and second phalanx or the first phalanx and the joint connected to it. Thus an improved contact between the finger and the splint can occur in a simple manner. In addition, the fingerstall can be unreinforced in its material as before.

It is preferably provided that the detachable fastener is a VELCRO® hook-and-loop fastener. This enables simple handling. In addition, such a VELCRO® hook-and-loop fastener is robust, so that such a therapy glove is also suitable for washing in a washing machine.

Furthermore, it is preferably provided that the each end of the hook- and strap band is firmly attached to the inelastic region of the fingerstall or the fixing pocket and that the opposite ends are fixed to the fixing pocket or the inelastic region of the fingerstall and provide the VELCRO® hook-and-loop fastener. This embodiment enables a band to be guided laterally along the elastically flexible region of the fingerstall in each case, such that a distance between the inelastic region on the fingerstall and the fixing pocket is reduced and the finger is thereby held fixed to the finger splint section.

According to an alternative embodiment, it is provided that the VELCRO® hook-and-loop fastener has a tab, with the hook- or strap band being provided on the respective end thereof, wherein the one end of the tab is fixed, in particular sewn on or glued, to the fixing pocket or the non-elastic region of the fingerstall, and the opposite end of the tab which complementary comprises the strap- or hook band can be connected to the first end of the tab. The tab can thereby be guided once around the fingerstall with the fixing pocket in order to fix the tab. This allows one-hand operation.

The hook- and strap band can be provided on a finger outer side according to a first embodiment. Alternatively, the hook- and strap band can also be fixable to a finger inner side, such that the detachable fastener is situated opposite the fixing of the hook- and strap region.

Furthermore, it can be provided that the detachable fastener is provided opposite the fixing pocket for the fixing splint on the fingerstall. The detachable fastener can also be arranged directly on the fixing pocket into which the finger splint section can be inserted.

Advantageously, the therapy glove has a fixing splint with at least one finger splint section, which has an elongated recess. The contact of the finger to the splint can be further improved due to this elongated recess. An inner side of the finger can slightly engage in the recess, such that the finger can be received and guided by two-sided splints which are formed by the recess in the finger splint section.

The elongated recess in the finger splint section preferably follows an outer contour of the finger splint section. A peripheral web is formed in this way. This peripheral web is preferably formed with a constant width. This shows a design which is easy to manufacture. In addition, a comfortable support of the finger is available for the user.

Furthermore, it is preferably provided that the width of web is narrower than the width of the elongated recess. As well as the support comfort, this also has the advantage that a bending on one of the finger splint sections can be easily introduced if necessary.

An alternative design of the elongated recess in the finger splint section provides that, seen in longitudinal extension, two bulbous contours are provided in the region of the joints between the first and second phalanx and the second and third phalanx. This can result in a slight bulging or widening of the elongated recess, such that the support comfort can be increased further.

Furthermore, it is preferably provided that at least one free recess is provided in the main splint section of the fixing splint. A further weight saving of the therapy glove can thereby be enabled and thus an improvement of the support comfort can be available.

The fixing splint, consisting of the main splint section and at least one finger splint section, is preferably formed as a stamped part. This enables simple manufacturing. In particular, the fixing splints are made of an aluminium sheet frame. The fixing splints are preferably provided with a varnish or coating. Alternatively, the fixing splint can also be manufactured from plastic, in particular a plastic which can be deformed by heat. Such support splints can also be manufactured from a metallic material or plastic in a 3D printing process. Individual adjustments to the size of the hand and the finger of the user can thereby easily be enabled. Furthermore, it can be provided that the fixing splint is manufactured from a fibre-reinforced plastic, such as a glass fibre-reinforced or carbon fibre-reinforced plastic.

The object underlying the invention is furthermore solved by a fixing splint for a therapy glove, in particular according to one of the embodiments described above, in which the at least one finger splint section has an elongated recess. An improved arrangement of the finger on the finger splint section can thereby be enabled. A single linear support, which can lead to pressure marks, is prevented. The elongated recess in the finger splint section of the fixing splint preferably runs along an outer contour of the finger splint section. A peripheral web can thereby be formed, such that the finger can lie on two webs spaced apart from each other.

The width of the web on the finger splint section is preferably narrower than the width of the elongated recess. The support comfort can thereby be improved.

In particular, the recess in the finger splint sections has one or two bulbous contours in longitudinal extension, which are provided in the region of the joints between the first and second phalanx and/or the second and third phalanx.

At least one free recess can also be provided in the splint section of the fixing splint. This forms a weight reduction.

According to an embodiment, the fixing splint with the main splint section on the at least one finger splint section can be formed as a stamped part. Alternatively, manufacturing from plastic, in particular a fibre-reinforced or a heat-deformable plastic, can also be provided.

The invention as well as further advantageous embodiments and developments of the same are described in more detail and explained hereinafter with the examples shown in the drawings. The features to be derived from the description and the drawings can be applied individually or in any kind of combination according to the invention. Here are shown:

FIG. 1 a schematic view of a therapy glove having a fixing splint after being put on the hand of a patient.

Figure 2:
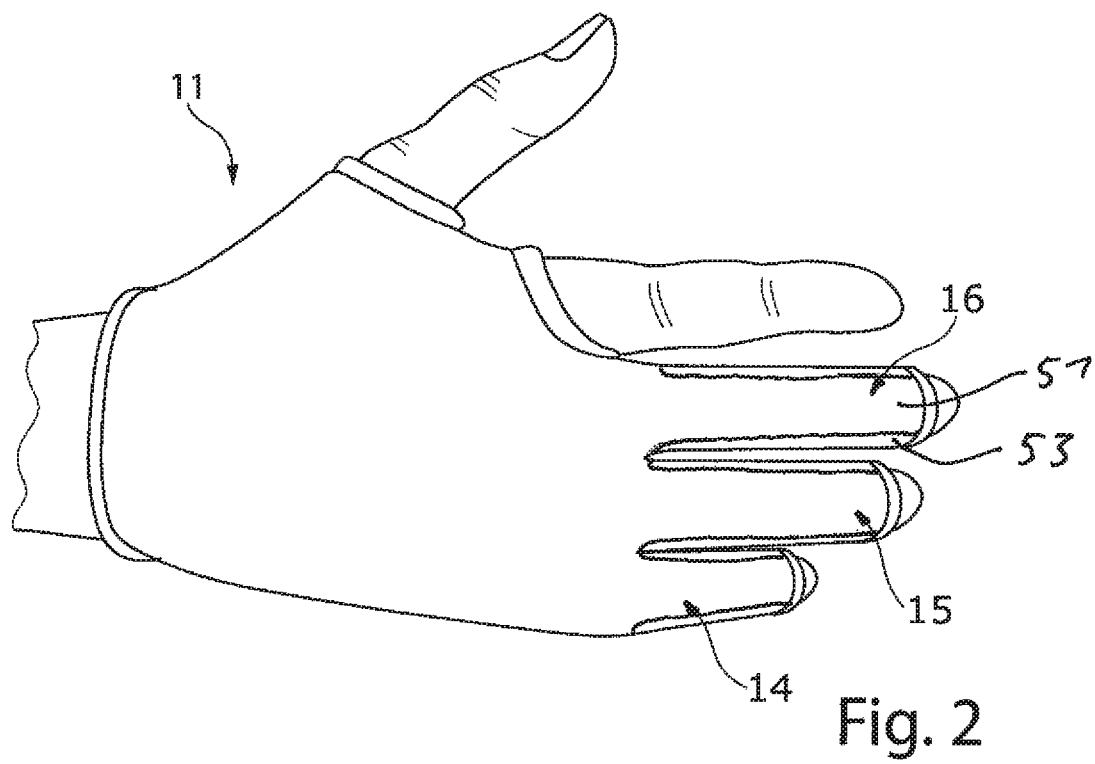
Figure 3:
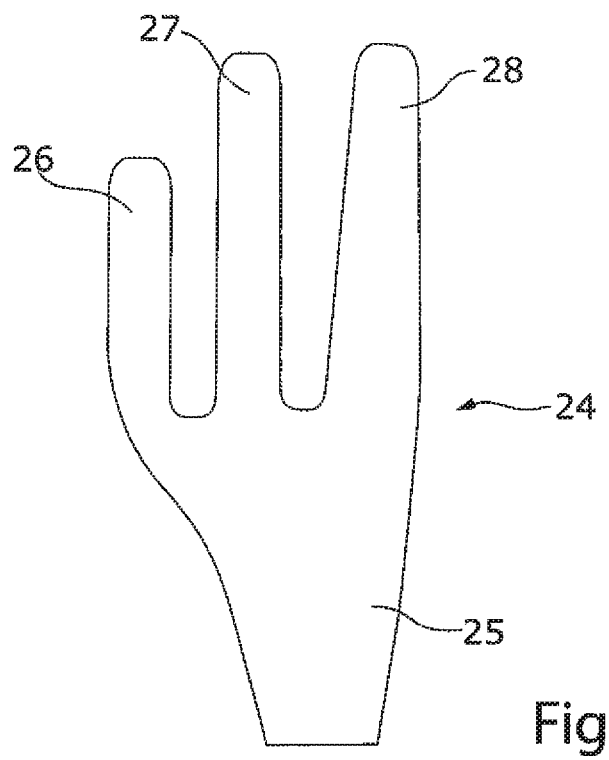
Figure 4:
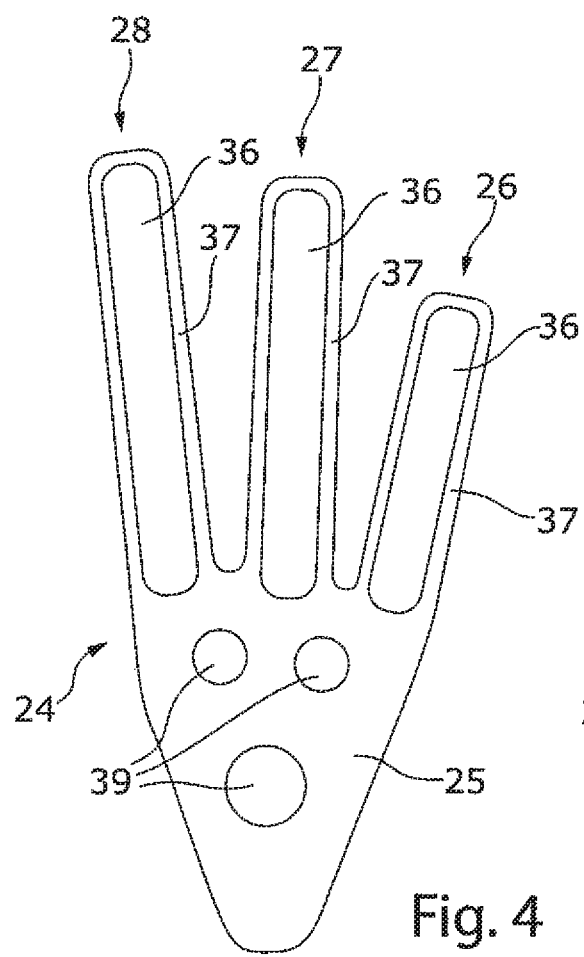
Figure 5:
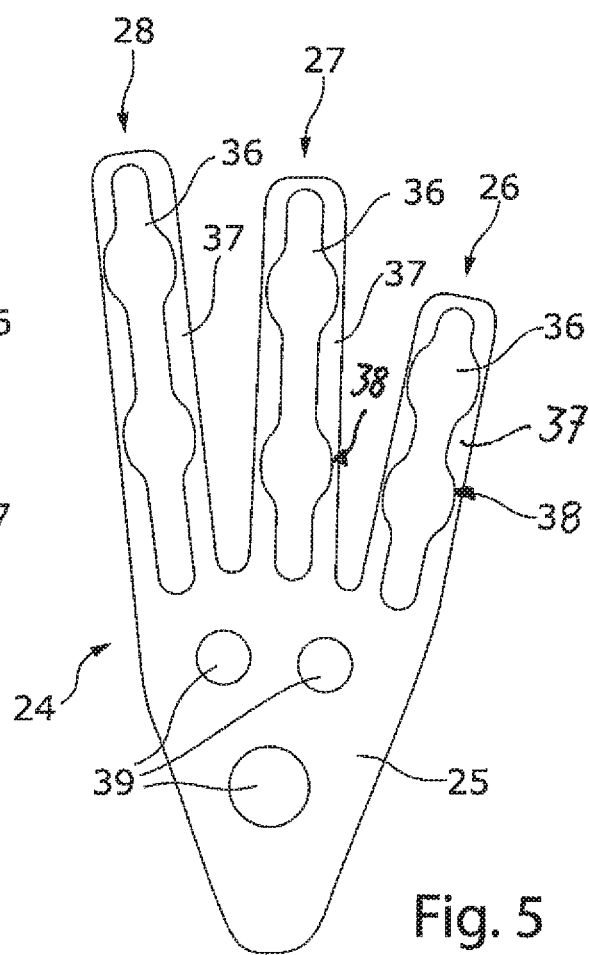
Figure 6:
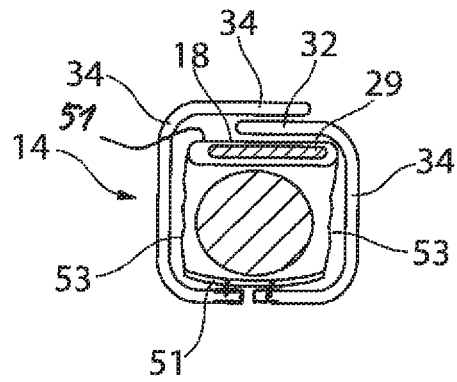
Figure 7:
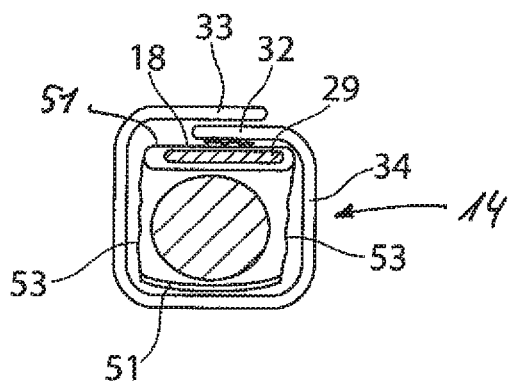
Figure 8:
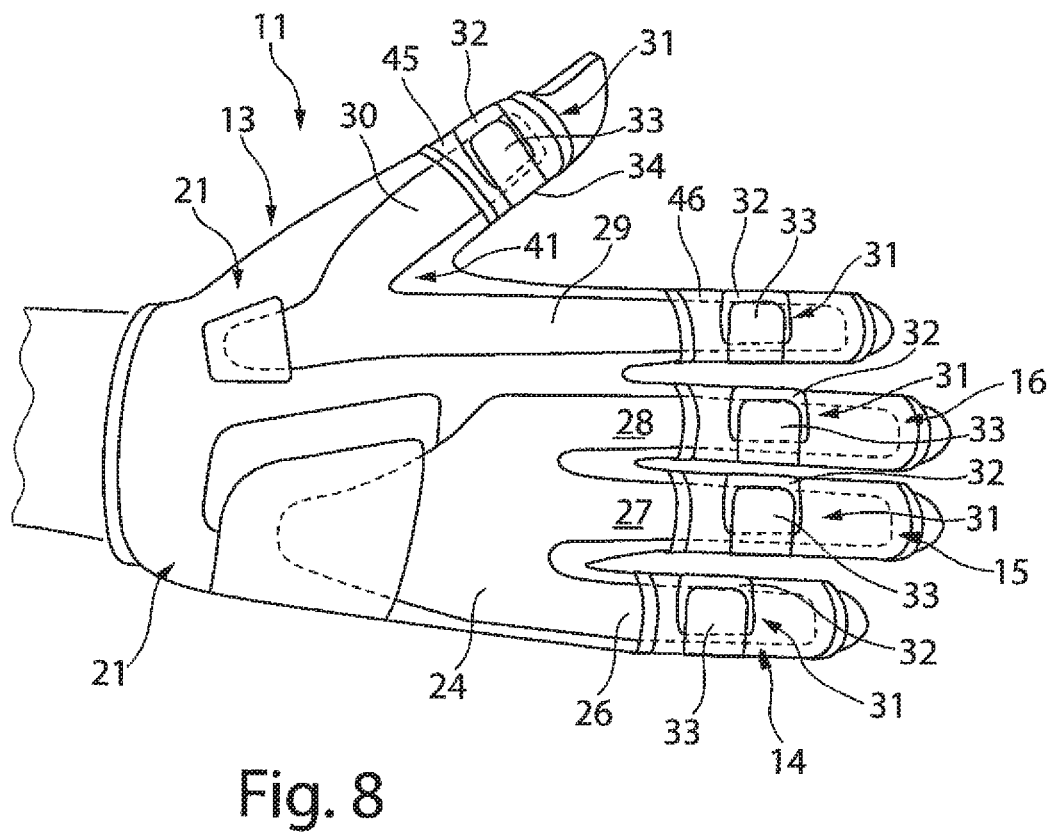

FIG. 2 a schematic view of an inner side of the therapy glove according to FIG. 1, FIG. 3 a schematic view of the fixing splint in the therapy glove according to FIG. 1, FIG. 4 a schematic view of an alternative embodiment to FIG. 3 of the fixing splint, FIG. 5 a schematic view of an alternative embodiment to FIG. 4 of the fixing splint, FIG. 6 a schematic sectional view along the line V-V in FIG. 1, FIG. 7 a schematic sectional view of an alternative embodiment to FIG. 6, and FIG. 8 a schematic view of an inner side of a therapy glove according to an alternative embodiment to FIG. 1 after being put on the hand of a patient.

In FIG. 1, a first embodiment of a therapy glove 11 is shown. This therapy glove 11 is put on a hand of a patient. The therapy glove 11 comprises a glove 13 having a central region 12, which reaches across the back of the hand according to FIG. 1 as well as across the palm of the hand according to FIG. 2. Three fingerstalls 14, 15, 16 extend outwards from this central region 12. These serve to accommodate the little finger, the ring finger and the middle finger.

The therapy glove 11 has fixing pockets 18 on its outer side of the fingerstalls 14, 15, 16. These comprise an insertion opening 19, which is oriented towards the central region 12. In the region of the back of the hand, a detachable fastening means 21 is provided.

A fixing splint 24 according to FIG. 3 comprises a main splint section 25, on which three finger splint sections 26, 27, 28 extend. These finger splint sections 26, 27, 28 have a progression to be assigned to the little finger, middle finger and the ring finger. Such a fixing splint 24 is manufactured from a plate-like material. This can preferably be a metal sheet, in particular an aluminium sheet. Alternatively, a plastic can be used. A heat-deformable plastic or a fibre-reinforced plastic can also be used.

This fixing splint 24 is fixed in the therapy glove 11 on the back of the hand according to FIG. 1. The finger sections 26, 27, 28 are inserted into the fixing pockets 18 of the fingerstalls 14, 15, 16. Subsequently, the main splint section 25 can be held in place by the fastening means 21 formed as a detachable fastener.

This arrangement enables a desired therapeutic stretching position of the finger or fingers with the fixing splint 24.

For the installation of the finger or fingers in the fingerstall(s) 14, 15, 16 on the respective finger splint section 26, 27, 28, a detachable fastener 31 is provided on each fingerstall 14, 15, 16. This detachable fastener 31 is arranged on the fingerstall 14, 15, 16 in the region of the first phalanx. Alternatively, the detachable fastener 31 can also be provided in the region of the joint between the first and second phalanx. The detachable fastener 31 can be formed to be wide, such that this covers a part of the first phalanx and the joint between the first and second phalanx.

The detachable fastener 31 on the fingerstalls 14, 15, 16 is preferably formed as a VELCRO® hook-and-loop fastener, which comprises a hook band 32 and a strap band 33. The hook band 32 is preferably directly fixed to the fingerstall 14, 15, 16, in particular sewn or glued on. The strap band 33 is provided on a tab 34, wherein the tab 34 is fixed at a distance from the hook band 32 on the fingerstall 14, 15, 16 or on an end of the hook band 32.

It is understood that the arrangement of the hook band and strap band 32, 33 can be interchangeably arranged for the above-described example as well as for the subsequent examples.

The arrangement of the strap band 33 and the tab 34 enables the strap band 33 to be arranged in different positions relative to the hook band 32. Thus the user can adjust the position of the finger on the finger splint section 26, 27, 28. In particular, this ensures that the finger lies on the finger splint section 26, 27, 28 and cannot lift off.

Due to the attaching of the hook band 32 to the fingerstall 14, 15, 16, a simple one-hand operation can be enabled.

In the embodiment according to FIG. 1, the fixing splint 24 is assigned to the back of the hand. The detachable fastener 31 of the respective fingerstall 14, 15, 16 is also arranged on an outer side of the finger. Alternatively, it can be provided that the detachable fastener 31 is also provided on the inner side of the fingerstall 14, 15, 16.

A further embodiment of the therapy glove 11, which is not shown, can consist in that the fixing pockets 18 as well as the detachable fastening means 21 are arranged on the inner side of the hand. The detachable fasteners 31 on the fingerstalls 14, 15, 16 can also be provided on the inner side or else again for easy operation on the outer side of the fingerstalls 14, 15, 16.

In FIG. 4, an alternative embodiment to FIG. 3 of a fixing splint 24 is shown. This fixing splint 24 comprises a main splint section 25, from which finger splint sections 26, 27, 28 extend outwards. By way of example, three finger splints sections 26, 27, 28 are shown. On the main splint section 25, only one or two finger sections or even four finger sections can also be provided.

In the respective finger splint section 26, 27, 28, an elongated recess 36 is provided. This elongated recess 36 preferably extends along the whole fixing splint section 26, 27, 28. Thus in comparison to the embodiment in FIG. 3, the fixing splint section 26, 27, 28 does not have any flat support for the respective finger. Rather, a peripheral web 37 is formed, which forms the finger splint section 26, 27, 28. This web 37 is preferably provided in a progression with a constant width.

In the shown exemplary embodiment according to FIG. 4, the recess 36 is formed to be elongated and rectangular with round corners. Alternatively, the recess 36 can also have an inner contour. By way of example, this can be bulbous, such that an inner edge of the recess 36 follows an outer contour of the finger. By way of example, two bulbous sections can be provided in the region of the joints.

Advantageously, one or several free recesses 39 are provided in the main splint section 25. These can be arbitrary in contour, in arrangement and/or in number. The free recesses 39 serve to save weight.

In FIG. 5, a schematic view of an alternative embodiment to FIG. 4 of the fixing splint 24 is shown. In this embodiment, it is provided that the recess 36 comprises at least one, preferably two, bulbous contours 38, which are provided in the region of the joints between the first and second phalanx, or second and third phalanx. The support comfort is thereby increased. In addition, an improved contact of the finger to the fixing splint 24 can be adjusted by means of the detachable fastener 31.

In FIG. 6, a schematic sectional view along the line V-V in FIG. 1 is shown. In this embodiment, it is provided that the fixing pocket 18 is formed from an inelastic material or non-flexible material. The form of the fixing pocket 18 is maintained after the finger splint section 26, 27, 28, 29, 30 is inserted. The fingerstall 14, 15, 16, 46, 47 is sewn on to this fixing pocket 18. This fingerstall 14, 15, 16, 46, 47 at least sectionally consists of an elastically flexible material. The whole fingerstall 14, 15, 16, 46, 47 can, for example, consist of an elastically flexible material, whereby putting on the therapy glove is made easier. In the case of the embodiment according to FIG. 6, it is preferably provided that a region 51 of the fingerstall 14, 15, 16 opposite the fixing pocket 18 consists of an inelastic material or non-flexible material and the sections or regions 53 extending between the fixing pocket and the inelastic region 51 consist of an elastically flexible material. In this embodiment too, it is easier to put on the therapy glove 11, since a widening of the fingerstall between the fixing pocket 18 and the inelastic region 51 opposite is possible.

The inelastic and non-elastic region can consist of a fabric, in particular a cloth fabric, or knitted fabric or artificial leather or natural leather. The elastically flexible region can consist of a rubber-elastic fabric or very stretchable material or a material containing elastane.

In this embodiment according to FIG. 6, it is provided, for example, that the detachable fastener 31 as a VELCRO® hook-and-loop fastener. This detachable fastener 31 comprises a tab 34 with a hook band 32 and a tab 34 with a strap band 33. The respective ends of the tab 34, in which the hook- and strap band 32, 33 hook into each other, are, for example, assigned to the fixing pocket 18. The opposite ends of the respective tab 34 are securely fixed on the inelastic region 51 of the fingerstall 14, 15, 16, 46, 47. This can occur by sewing on and/or gluing on and/or welding. Only one tab 34 can be provided, which has a hook- and strap band 32, 33 on the respective end and in the middle region is fixed on the inelastic region 51 of the fingerstall 14, 15, 16, 46, 47 or on the fixing pocket 18. In the case of these embodiments, it is provided that the inelastic region 21 and the fixing pocket 18 are moved towards each other when the hook- and strap band 32, 33 are being fixed, whereby an extension of the finger in the fingerstall 14, 15, 16, 46, 47 relative to the fixing splint 24 is obtained.

In FIG. 7, an alternative embodiment to FIG. 6 is shown. The structure of the fingerstall 14, 15, 16, 46, 47 having the insertion pocket 18 arranged on it corresponds to the embodiment according to FIG. 6. Deviating from this, it is provided that the hook- and strap band 32, 33 is provided on the respective end of a single tab 34, wherein an end of the tab 34 is firmly connected to the fixing pocket 18 or to the inelastic region 51 of the fingerstall 14, 15, 16, 46, 47. Thus the strap band 33 can be fixed to the hook band 32, for example, using a hand. An exchange is also impossible.

In FIG. 8, an alternative embodiment to FIG. 1 of the therapy glove 11 is shown. In this embodiment, the fixing splint 24 is detachably fixed to an inner side of the hand. The fixing pockets 18 are provided on the inner side of the finger. The detachable fastening element 21 is provided in the region of the palm of the hand.

In this embodiment according to FIG. 8, a second fixing splint 41 is provided. This fixing splint 41 has a finger splint section 29 for an index finger and a finger splint section 30 for a thumb. The glove 13 additionally has a fingerstall 46 for the thumb and a fingerstall 47 for the index finger. On each fingerstall 46, 47, a fixing pocket 18 is preferably provided. The finger splint sections 29, 30 can preferably be inserted into fixing pockets 18. Opposite these, a pocket or a detachable fastening element 21 is provided, in order to fix these fixing splints 41 in the region of the heel of the hand.

On the fingerstalls 46, 47, as with the fingerstalls 14, 15, 16, a detachable fastener 31 is provided in each case. The functioning and the possible embodiments of the detachable fastener 31 correspond to those described for the therapy glove 11 according to FIGS. 1 to 4.

The therapy glove 11 can be manufactured from leather or an elastic plastic material which can have a perforation like leather. Alternatively, the elastic plastic material can also be breathable.

The invention claimed is:

1. Therapy glove for fixing at least one finger,
   having a glove which comprises a central region, which encloses the back of a hand and/or the palm of a hand,
   having, going outwards from the central region, at least one fingerstall in which the finger is fixable accommodated,
   having at least one fixing splint, which has a main splint section and at least one finger splint section arranged on it,
   having at least one fixing pocket arranged on the fingerstall, into which the finger splint section is insertable,
   having a fastening element in the central region, by means of which the fixing splint is detachably fastened, wherein the fixing splint, which is inserted into the finger pocket and held by fastening means, fixes the finger accommodated in the fingerstall in a therapy position relative to the back of the hand,
   wherein
   on every fingerstall which has a fixing pocket, a detachable fastener is provided, by means of which a contact position of the finger in the fingerstall is adjustable relative to the finger splint section, and
   the fingerstall is formed at least in sections from an elastically flexible material and the fixing pocket consists of an inelastic material, and the fingerstall has a region made from inelastic material opposite the fixing pocket, which is oriented towards the inner or outer side of the hand, and an elastically flexible region is formed between the inelastic region of the fingerstall and the fixing pocket.

2. Therapy glove according to claim 1, wherein the detachable fastener is a hook-and-loop fastener.

3. Therapy glove according to claim 2, wherein the hook-and-loop fastener has a hook- and strap band and which are securely provided on an inelastic region of the fingerstall or the fixing pocket and are fixable to each other on the fixing pocket or the inelastic region.

4. Therapy glove according to claim 2, wherein the hook and loop fastener comprises a tab, which provides on each end of a tab a hook- and strap band and an end of the tab is fixed to the fixing pocket or the inelastic region of the fingerstall and the tab enclosing the fingerstall and the free end of the tab can be fixed on the fixed end of the tab.

5. Fixing splint for a therapy glove according to claim 1,
   having a main splint section and one or several finger splint sections arranged on it,
   having at least one elongated recess in the finger splint section
   wherein
   the elongated recess follows in the outer contour of the finger splint section and the finger splint section has a peripheral web, or
   the elongated recess has one or two bulbous contours in the finger splint section in longitudinal extension, which are provided in the region of the joints between the first and second phalanx and/or the second and third phalanx.

6. Fixing splint according to claim 5, wherein at least one free recess is provided in the main splint section of the fixing splint.

7. Fixing splint according to claim 5, wherein the fixing splint is manufactured as a stamped part or is made from a plastic, in particular a fibre-reinforced plastic, or from a plastic which can be deformed by being heated.

8. Therapy glove according to claim 1, wherein the detachable fastener is provided in the region of the first or second phalanx or in the region of the joint between the first and second phalanx or overlapping the first and second phalanx and the joint between them.

9. Therapy glove according to one claim 1, wherein the fixing splint can be fixed in fixing pockets in contact with the back of a hand or in contact with the inner side of a hand.

10. Therapy glove according to claim 1, wherein the at least one finger splint section has an elongated recess, which follows in the outer contour of the finger splint section and the finger splint section has a peripheral web, or which has one or two bulbous contours in the finger splint section in longitudinal extension, which are provided in the region of the joints between the first and second phalanx and/or the second and third phalanx.

11. Therapy glove according to claim 1, wherein at least one free recess is provided in the main splint section of the fixing splint.

12. Therapy glove according to claim 1, wherein the fixing splint is manufactured as a stamped part or is made from a plastic, in particular a fibre-reinforced plastic, or from a plastic which can be deformed by being heated.

* * * * *